United States Patent [19]

Chang

[11] Patent Number: 5,383,866
[45] Date of Patent: Jan. 24, 1995

[54] OCCLUSION URETERAL CATHETER FOR RETROGRADE PYELOGRAPHY

[76] Inventor: Hau H. Chang, 7704 Calle Espada, Bakersfield, Calif. 93309

[21] Appl. No.: 120,796

[22] Filed: Sep. 15, 1993

[51] Int. Cl.$^6$ .......................................... A61M 25/00
[52] U.S. Cl. .................... 604/280; 604/175; 604/278
[58] Field of Search ............ 604/93, 171–175, 604/276, 278, 280, 284; 128/DIG. 25

[56] References Cited

U.S. PATENT DOCUMENTS

| | | | |
|---|---|---|---|
| 3,394,705 | 7/1968 | Abramson | 604/278 |
| 3,630,206 | 12/1971 | Gingold | 604/102 |
| 3,721,229 | 3/1973 | Panzer | 604/278 |
| 3,927,672 | 12/1975 | Garcia | 604/278 |
| 4,133,303 | 1/1979 | Patel | 604/280 |
| 4,237,894 | 12/1980 | Cohen | 604/280 |
| 4,432,758 | 2/1984 | Finegold | 604/278 |
| 4,687,471 | 8/1987 | Twardowski | 604/280 |
| 4,959,057 | 12/1990 | Lang | 604/280 |
| 5,033,998 | 7/1991 | Corday | 604/280 |
| 5,096,454 | 3/1992 | Samples | 604/102 |
| 5,195,964 | 3/1993 | Kletzky | 604/278 |

*Primary Examiner*—C. Fred Rosenbaum
*Assistant Examiner*—Chalin Smith

[57] ABSTRACT

The occlusion ureteral catheter for retrograde pyelography with a compression plate is a long slender catheter made of polyurethane radio opaque or any equivalent material. It has a central lumen which opens to both ends of the catheter. The catheter has three parts: the tip or head of the catheter, compression plate and the stem of the catheter. There are structural variations on the tip of the catheter and compression plate.

The tip of catheter has various shapes (whistle tip shape, cone or cobra head shape, olive tip shape and filiform shape), curvatures and sizes. The compression plate has various shapes (oval, circular, triangular) sizes and angulations. The compression plate is fixed and an integral part of the stem of the ureteral catheter. The occlusion ureteral catheter for retrograde pyelography comprises of a serial of catheters with structural variation at the tip and the compression plate.

The occlusion ureteral catheter for retrograde pyelography is manufactured to adapt to conventional cystoscopic or flexible endoscopic instructions.

The primary function of the occlusion ureteral catheter for retrograde pyelography is to create a watertight seal by compressing at the mucosa surrounding the ureteral orifice to prevent retrograde leakage of the contrast from the ureter to the urinary bladder, to produce an efficient positive pressure filling of the ureter and to reduce the radiation exposure to the patient, operator and personnel.

8 Claims, 4 Drawing Sheets

Fig. 1
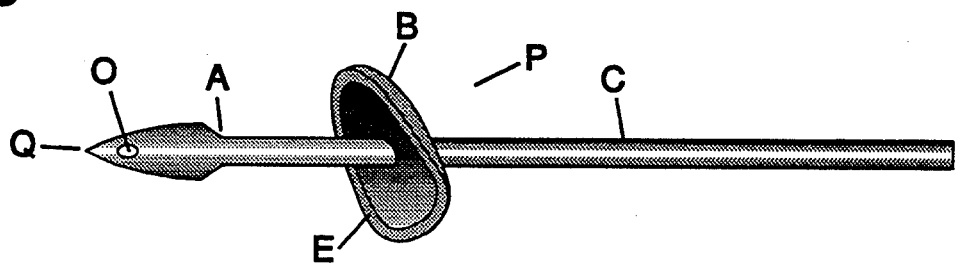
Fig. 2
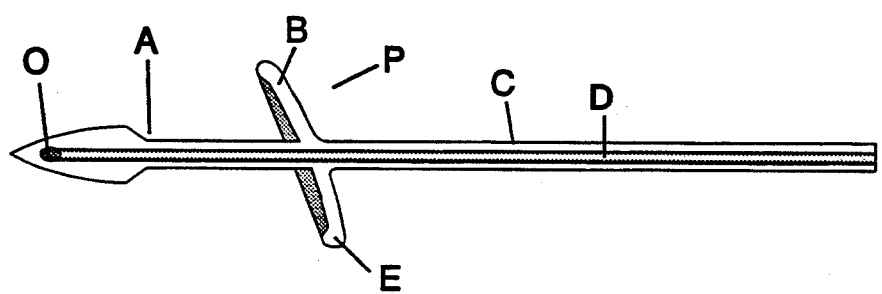
Fig. 3
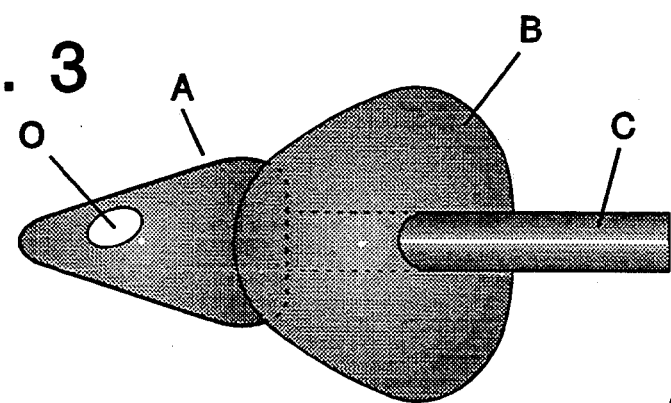
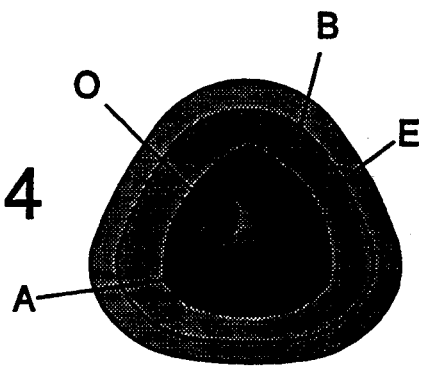
Fig. 4

OCCLUSION URETERAL CATHETER FOR RETROGRADE PYELOGRAPHY

BACKGROUND OF THE INVENTION

1. Field of the Invention

The invention relates to an ureteral catheter which compresses the ureteral orifice at ureterovesical junction through the bladder at the time of cystoscopic examination and retrograde pyelogram. The purpose is to prevent the leakage of the injected iodinated contrast from the ureteral orifice back to the bladder cavity. It improves the quality of the retrograde pyelogram film and facilitates the efficiency of the procedure. From time to time, most practicing urologist have had experience with incomplete occlusion of the ureteral orifice with a cone tip ureteral catheter during the procedure of retrograde pyelography. As the result, the ureter cannot be sufficiently filled with pressure to distend the portion of the ureter or renal collecting system in question. This is especially true in patients with large patulous ureteral orifice or dilated intramural portion of ureter.

In contrast, in a situation when a patient has ureteral orifice too small to accomodate the conventional cone tip ureteral catheter or a segment of whistle tip, or spiral tip ureteral catheter, or in a situation when the distal ureter is angulated from the ureteral catheter, retrograde pylegraphy will be very difficult or impossible.

To overcome these difficulties, a compression shield, or a small occlusion plate is constructed at approximately half to two centimeters proximal to the tip of the ureteral catheter. The plate on the ureteral catheter is used to compress the bladder mucosa around the ureteral orifice. It prevents the leakage of the injected contrast back to the bladder cavity in a patulous ureteral orifice.

It provides a tight seal around a high pressure space and forces the contrast to flow into the ureter in a small or angulated ureteral orifice when it is difficult to cannulate.

2. Description of the Prior Art

Cystoscopic examination and retrograde pyelogram is a common urological procedure. It provides adequate visualization of the ureter. The procedure is usually performed to a patient in the following conditions:
1. When conventional intravenous pyelogram cannot sufficiently opacify or fill the ureter precluding an adequate diagnosis of the ureteral pathology.
2. When patient has medical conditions not suitable the usage of intravenous injection of iodinated contrast. This includes patient with previous history of iodinated contrast allergy, azotemia, multiple myeloma, etc.
3. To identify the fistula, calculus, tumor, or structural abnormality of the ureter.

Most retrograde pyelography can be adequately performed with the conventional ureteral catheters available to date. The ureteral catheters with whistle tip, flexible whistle tip, cone tip, spiral tip, olive tip is commonly used. When using these catheters there are however significant leakage of the contrast from the ureter to the bladder cavity as the ureter is not tightly occluded by these catheters rendering the procedure inefficient, difficult and time consuming. When the ureter is poorly or inadequately filled in the areas in question, the procedures have to be repeated and a X-ray be taken. It therefore increases the chance of excessive radiation exposure to patient, operator and the nurses. There has been no catheter that can occlude the ureteral orifice by compressing the bladder mucosa around the ureteral orifice available to date.

SUMMARY OF THE INVENTION

Occlusion ureteral catheter is a long flexible slender radio opaque catheter with a small lumen in the center of the catheter. It has a blunt tip at one end of the catheter and a sharp cut edge at the other end of the catheter, the lumen courses the entire length and it opens at both ends of the catheter; the blind ended tip of the catheter can be manufactured in different shapes, curvatures and sizes. The size or diameter of the catheter is measured in French, usually ranging from 3 F. to 10 F., most commonly 4 to 8 F. There is a small compression plate at approximately 0.5-2 cms proximal to the blunt end of the ureteral catheter. The size of the plate is usually a few minimeter in diameter. The shape of the plate can be round, oval or triangular. The size and shape of the plate is constructed so that it will cover the ureteral orifice from the urinary bladder. There is a elevated edge at the peripherey of the plate. The edge will produce a tight seal when the plate compresses against the bladder mucosa around the ureteral orifice as the contrast is injected, a high pressure is produced during the retrograde pyelogram.

The entire ureteral catheter can be threaded through the working port of the currently available cystoscopic instruments.

If the compression plate is too large to be threaded through the working port of the cystoscopic instruments in antegrade manner, the catheter can be threaded into cystoscope in the retrograde manner from the sharp edge end. The blunt end of the catheter has a small opening, it communicates with the lumen of the ureteral catheter, the opening can be at the very tip or on the side of the blunt end tip. The shape of the tip of the catheter varies from whistle shape, olive shape, cone or cobra head shape or spiral shape. The size and curvature of the tip are also varied. The tip of the catheter can be straight or curved. The compression plate at one end of the ureteral catheter is angulated at different angles to the long axis of the ureteral catheter; the usual angle is 45 degrees. The material, size and shape of the present catheter is not different from the conventional retrograde ureteral catheter. What is different is the presence of compression plate at the blunt end of the ureteral catheter suitable for high pressure retrograde pyelography. The objective of this new modified improved version of this ureteral catheter is to prevent the leakage of the contrast from the ureteral orifice to the urinary bladder. The phenomenon commonly occurs in the presently available retrograde ureteral catheter. It produces higher quality of retrograde pyelouretero-gram, reduces the number of the retrograde pyelogram film needs to be taken (compares to the conventional catheter) and radiation exposures to operator, patient and all personel in the operating room.

BRIEF DESCRIPTION OF THE DRAWING

The occlusion ureteral catheter for retrograde pyelography in accordance with the present invention will now be described by way of examples with reference to the accompanying drawing:

FIG. 1 is a external side view of the cobra head (or cone tip) occlusion ureteral catheter with occlusion plate angulated.

FIG. 2 is a longitudinal section view of the cobra head (or cone tip) occlusion ureteral catheter with occlusion plate angulated.

FIG. 3 is a oblique external view of FIG. 1 from right upper direction.

FIG. 4 is a head on view of FIG. 1 from left towards right direction.

DESCRIPTION OF THE PREFERRED EMBODIMENT

Referring to FIGS. 1, 2, 3, 4, 5, 6, 7, 8, 9, 10, 11, 12, 13, 14, 15 & 16 on the description of the drawings, a serial of embodiments of the occlusion ureteral catheter for retrograde pyelography are illustrated. The device is consisted of 1) a catheter tip of different size, shape and curvature as illustrated as A from FIG. 1 to 16. 2) a compression plate 0.5 to 2 cm proximal to the catheter tip with different size, shape and angulation from the long axis of the catheter as illustrated as B from FIG. 1 to 16. 3) a long catheter stem as illustrated as C from FIG. 1 to 16. 4) an inner lumen courses from one end of the catheter to the opposite end as illustrated as D in FIG. 2, 5, 6 and 7. An opening at the tip of the catheter is illustrated as "O". The catheter itself is flexible radiopaque and is made of any form material suitable for sterilization and radiography. There is a rim elevation at the outer edge of the compression plate on the surface facing the head of the catheter, as shown as E in FIGS. 1 to 16. The compression plate angled from axis of catheter ranging from 90 to zero degree.

Figure 16:
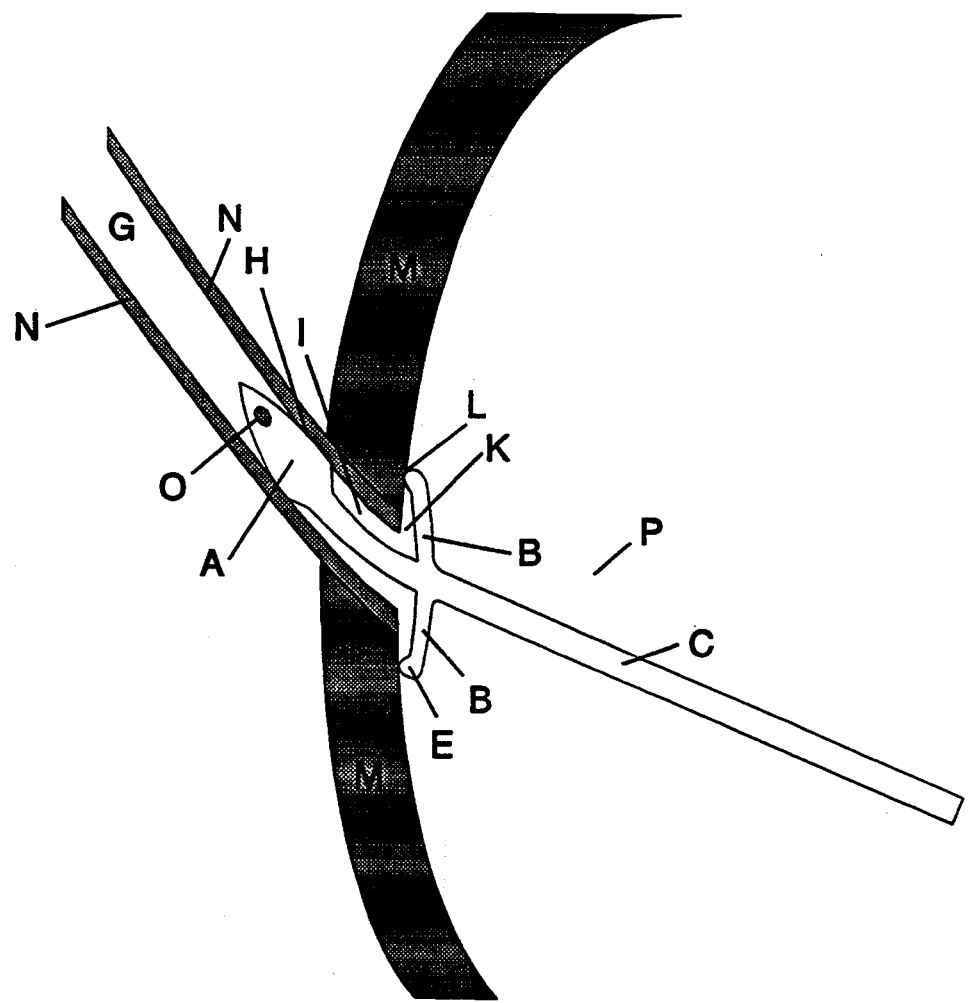
FIG. 16 is an illustration of clinical application showing the ureteral catheter tip in the distal ureter and the compression plate compressing the mucosa around the ureteral orifice.

FIG. 16 is an illustration of the clinical application of a 45 degree angle plate on a cone tip ureteral catheter at the time of retrograde pyelography noting that M represents urinary bladder muscular wall. N represents distal ureter. I represents intramural ureter. H represents contact point of tip of ureteral catheter to the intramural ureter. L represents circumferential pressure line by compression plate B on the bladder wall M.

In a conventional retrograde pyelography with a conventional ureteral catheter, as the iodinated contrast is injected into lumen G through opening O, it creates a high pressure in lumen G causing the contrast to leak out through H & I spaces. In a retrograde pyelography with the present invention, the leaking iodinated contrast is trapped within space K because of the pressure line L.

FIG. 1 illustrates an external side view of the straight cone tip angled compression plate ureteral catheter.

FIG. 2 illustrates the longitudinal section view of one of the variant of the compression plate ureteral catheter with a straight cone tip and a 45 degree angled compression plate proximal to the tip. Its external view is illustrated in FIG. 1.

FIG. 3 illustrates exteral view of the catheter in FIGS. 1 and 2 at the direction P.

FIG. 4 illustrates external view of the catheter in FIGS. 1 & 2 at the direction Q.

Figure 5:
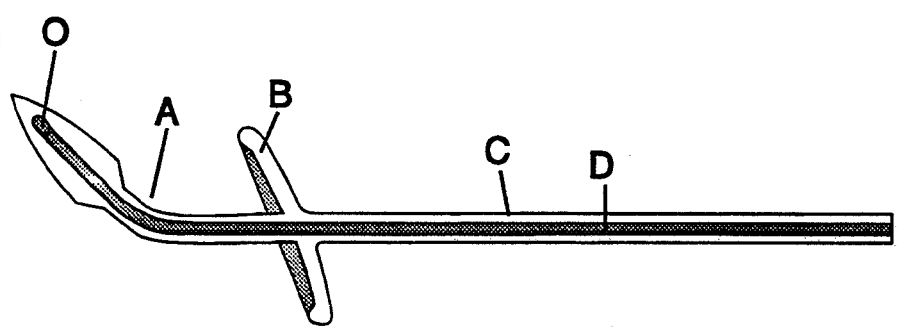
FIG. 5 illustrates longitudinal section view of a angled cone tip and occlusion plate ureteral catheter.
Figure 7:
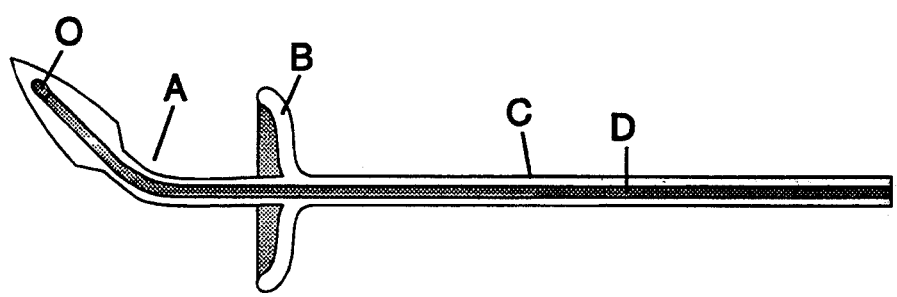
FIG. 7 is a longitudinal section view of a curved cone tip, right angle occlusion plate ureteral catheter.

FIGS. 5 & 7 illustrates the variants of the curved cone tip catheter with compression plate at 45 degree and 90 degree from the axis of the catheter respectively.

Figure 6:
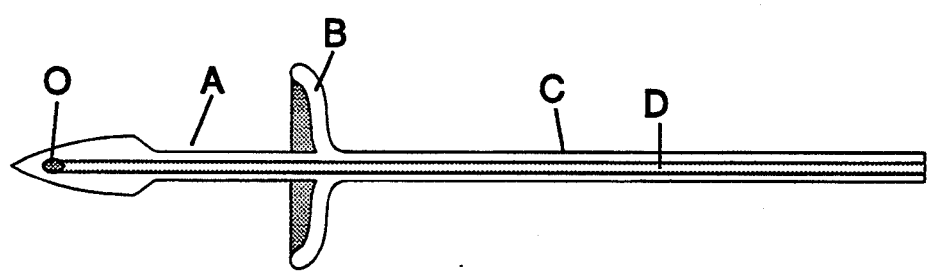
FIG. 6 is a longitudinal section view of a straight cone tip and right angle occlusion plate ureteral catheter.

FIG. 6 illustrates one of the variant of the catheter the same as in FIG. 2 except the compression plate is constructed at 90 degree from the axis of the catheter.

Figure 8:
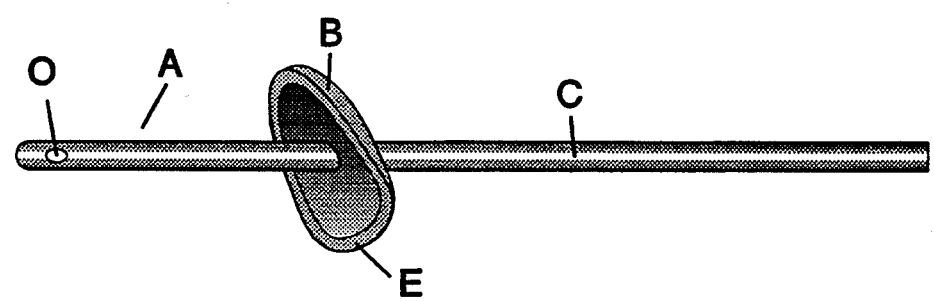
FIG. 8 is an external view of a straight whistle tip angled occlusion plate ureteral catheter.

FIG. 8 illustrates one of the variant of present series of invention with the tip of the catheter being whistle tipped and compression plate angled.

Figure 9:
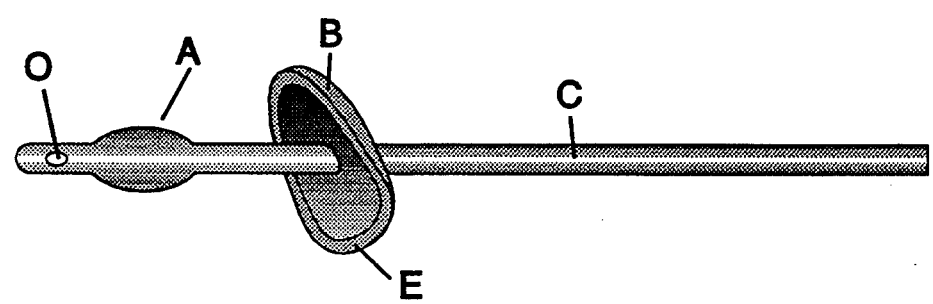
FIG. 9 is an external view of a straight olive tip angled occlusion plate ureteral catheter.

FIG. 9 illustrates one of the variant of present series of invention with the tip of the catheter being olive tipped, and the compression plate angled.

Figure 10:
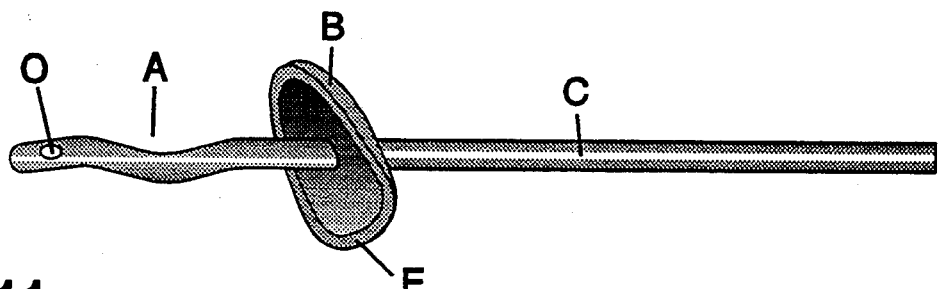
FIG. 10 is an external view of a straight spiral tip angled occlusion plate ureteral catheter.

FIG. 10 illustrates one of the variant of present series of invention with the tip of the catheter being spiral tipped and the compression plate angled from the axis of the catheter.

Figure 11:
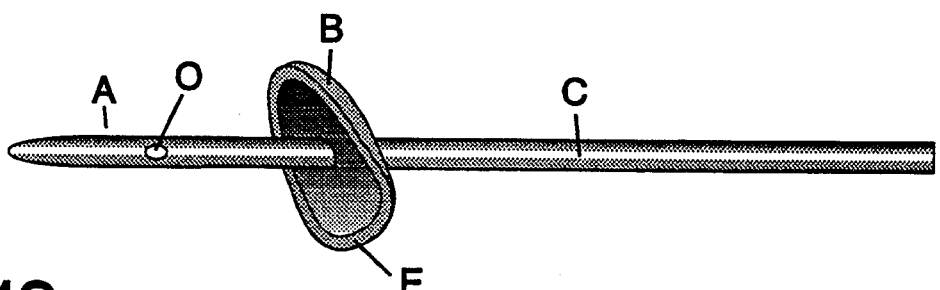
FIG. 11 is an external view of a straight filiform tip angled occlusion plate ureteral catheter.

FIG. 11 illustrates one of the variant of the present series of invention with the tip of the catheter being filiformed and the compression plate angled from the axis of the catheter.

Figure 12:
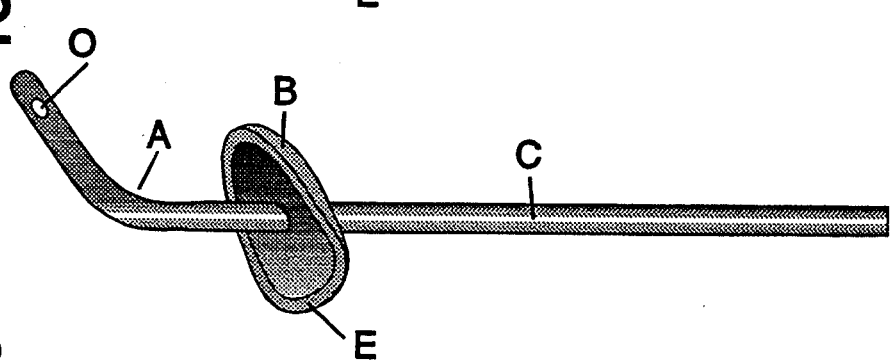
FIG. 12 is an external view of a curved whistle tip angled occlusion plate ureteral catheter.

FIG. 12 illustrates one of the variant of the present series of invention with the tip of the catheter being curve tipped and whistle tipped and compression plate being angled from the axis of the catheter.

Figure 13:
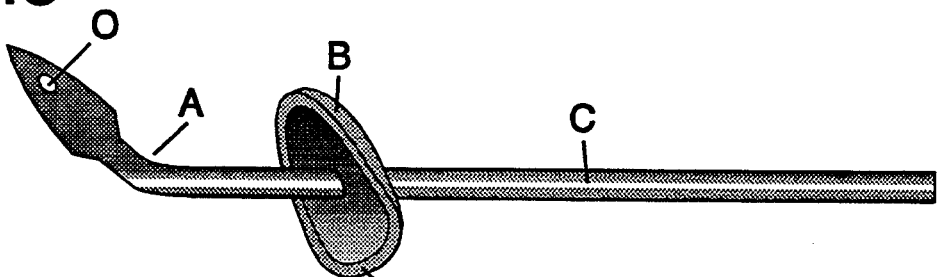
FIG. 13 is an external view of a curved cone tip angled occlusion plate ureteral catheter.

FIG. 13 illustrates one of the variant of the present series of invention with the tip of the catheter being curved and cobra headed and the compression plate being angled from the axis of the catheter.

Figure 14:
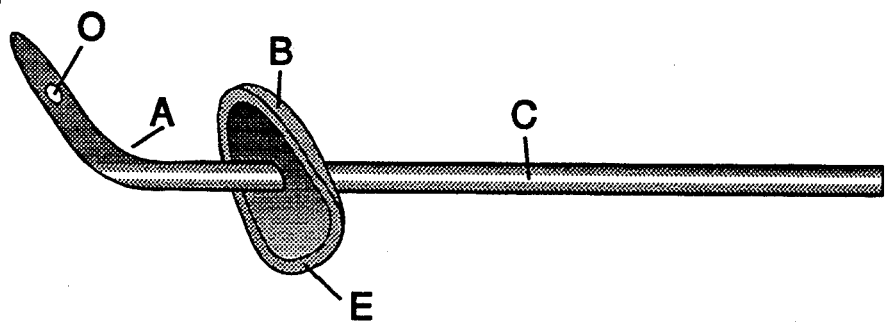
FIG. 14 is an external view of a curved filiform tip angled occlusion plate ureteral catheter.

FIG. 14 illustrates one of the variant of the present series of invention with the tip of the catheter being curved and filiformed, the compression plate being angled from the axis of the catheter.

Figure 15:
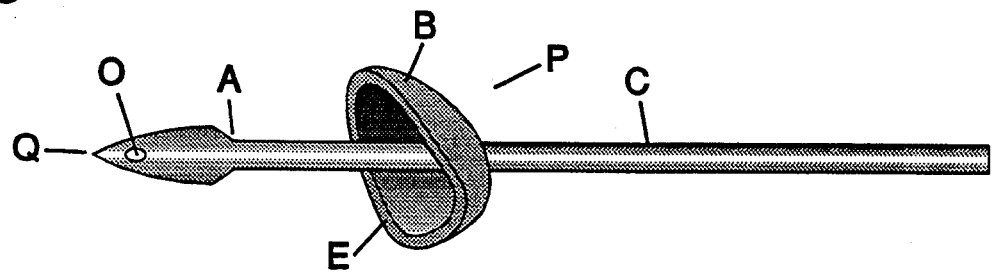
FIG. 15 is an external view of a straight cone tip and angled cupped compression plate ureteral catheter.

FIG. 15 illustrates one of the variant of the present series of invention with the tip of the catheter being cobra headed and the compression plate being angled and cupped.

FIGS. 8 through 15. The compression plate can be angulated between 90 degree to zero degree as their variant.

The present series of invention of occlusion ureteral catheter for retrograde pyelography consists of a flexible catheter with a lumen in the center running along it longitudinal axis. The lumen of the catheter opens at both ends of the catheter, a head of various size, shape and curvature at one end of the catheter, a compression plate proximal to the head of the catheter with an angulation from 90 degree to zero degree from the long axis of the catheter varies.

Although detail embodiments of the invention and their variants are illustrated in the drawings and previously described in detail, this invention contemplates any configuration, dimension, design and relationships of components which will function in a similar manner and which will provide the equivalent result.

I claim:

1. The occlusion ureteral catheter suitable for fitting the ureteral orifice through the urinary bladder at the uretero vesical junction through a cystoscope for retrograde pyelography, said catheter comprising:
   (a) a long, flexible slender radio-opaque catheter, said catheter comprising a head portion at its distal end and an elongate stem portion extending from the proximal end of said head portion, said catheter measuring less than 4 mm at its outer diameter, said catheter further comprising a smooth lumen extending therethrough from the distal tip of said head portion to the proximal end of said stem portion
   (b) a generally curved compression element comprising either a conical or plate shape, said compression element extending circumferentially around said catheter at a distance no greater than 2 cm from the tip of said head portion, the maximum diameter of said compression element larger than the maximum diameter of said head portion but less than 1 cm, said compression element further comprising an outer ridge portion at its outer circumference and a base portion, said ridge and base portions projecting toward the head portion of said catheter.

2. The occlusion ureteral catheter according to claim 1, wherein the distal tip of the head portion of the catheter is smooth and atraumatic and its shape is one of the group consisting of filiform, olive-shaped, acorn-shaped and spiralled.

3. The occlusion ureteral catheter according to claim 1 wherein the distal tip and the remainder of the head portion of the catheter can be straight or curved.

4. The occlusion ureteral catheter according to claim 1 wherein the compression element forms an angle with the longitudinal axis of the catheter ranging from zero to 90 degrees.

5. The occlusion ureteral catheter according to claim 1 wherein the shape of the compression element is one of the group consisting of triangular, ovoid, and circular.

6. The occlusion ureteral catheter according to claim 1 wherein said catheter is manufactured to be used in conjunction with a standard cystoscopic instrument.

7. The occlusion on ureteral catheter according to claim 1 characterized in that the compression plate and cup are an integraded fixed part of the catheter.

8. The occlusion ureteral catheter according to claim 1, wherein said catheter and compression element are made of radio opaque polyurethrane or any known equivalent material.

* * * * *